(12) United States Patent
Hu et al.

(10) Patent No.: US 9,592,186 B2
(45) Date of Patent: Mar. 14, 2017

(54) TOPICAL COMPOSITIONS AND METHODS FOR SKIN LIGHTENING

(71) Applicant: Avon Products, Inc., New York, NY (US)

(72) Inventors: Hong Hu, Basking Ridge, NJ (US); Sunghan Yim, Lincoln Park, NJ (US); Uma Santhanam, Tenafly, NJ (US); John W. Lyga, Basking Ridge, NJ (US)

(73) Assignee: Avon Products, Inc., Rye, NY (US)

( * ) Notice: Subject to any disclaimer, the term of this patent is extended or adjusted under 35 U.S.C. 154(b) by 257 days.

(21) Appl. No.: 14/409,607

(22) PCT Filed: Sep. 30, 2014

(86) PCT No.: PCT/US2014/058246
§ 371 (c)(1),
(2) Date: Dec. 19, 2014

(87) PCT Pub. No.: WO2016/053289
PCT Pub. Date: Apr. 7, 2016

(65) Prior Publication Data
US 2016/0263006 A1    Sep. 15, 2016

(51) Int. Cl.
*A61K 8/49*    (2006.01)
*A61Q 19/02*    (2006.01)
*A61K 8/46*    (2006.01)
*A61K 8/36*    (2006.01)
*A61K 8/06*    (2006.01)
*A61K 8/34*    (2006.01)
*A61K 8/67*    (2006.01)

(52) U.S. Cl.
CPC .............. *A61K 8/4926* (2013.01); *A61K 8/06* (2013.01); *A61K 8/062* (2013.01); *A61K 8/064* (2013.01); *A61K 8/342* (2013.01); *A61K 8/347* (2013.01); *A61K 8/36* (2013.01); *A61K 8/46* (2013.01); *A61K 8/675* (2013.01); *A61Q 19/02* (2013.01); *A61K 2800/42* (2013.01); *A61K 2800/48* (2013.01); *A61K 2800/522* (2013.01); *A61K 2800/524* (2013.01); *A61K 2800/54* (2013.01)

(58) Field of Classification Search
CPC .......................... A61Q 19/02; A61K 2800/42
See application file for complete search history.

(56) References Cited

U.S. PATENT DOCUMENTS

| | | | |
|---|---|---|---|
| 4,919,921 A | 4/1990 | Hatae | |
| 5,770,222 A | 6/1998 | Unger et al. | |
| 5,980,904 A | 11/1999 | Leverett et al. | |
| 6,245,795 B1 | 6/2001 | Takahashi et al. | |
| 6,352,699 B1 | 3/2002 | Mondet et al. | |
| 7,601,868 B2 | 10/2009 | Ishihara et al. | |
| 7,914,854 B2 | 3/2011 | Morita et al. | |
| 8,034,323 B2 | 10/2011 | Zheng et al. | |
| 8,329,149 B2 | 12/2012 | Lyga et al. | |
| 2010/0022585 A1* | 1/2010 | deLong ................ | C07D 217/02 514/312 |
| 2011/0092481 A1 | 4/2011 | Love et al. | |
| 2012/0177586 A1 | 7/2012 | Mehta et al. | |

FOREIGN PATENT DOCUMENTS

| | | |
|---|---|---|
| JP | 2001163759 A | 6/2001 |
| JP | 2001181173 A | 7/2001 |
| JP | 2003252743 A | 9/2003 |
| JP | 06-172321 * | 6/2006 |
| WO | 2006/055831 A2 | 5/2006 |
| WO | 2006/102289 A2 | 9/2006 |
| WO | WO 2006102289 A2 | 9/2006 |
| WO | 2014/158942 A1 | 10/2014 |
| WO | 2014/163896 A1 | 10/2014 |

OTHER PUBLICATIONS

Shin et al. JP 06-172321; published: Jun. 29, 2006; English machine translation obtained on Jan. 20, 2017.*
PubChem Compound-CID 24504067 create Date Feb. 29, 2008.

* cited by examiner

*Primary Examiner* — Ali Soroush
*Assistant Examiner* — Genevieve S Alley
(74) *Attorney, Agent, or Firm* — Brian P. McCloskey

(57) ABSTRACT

Embodiments of the invention are generally directed to compositions useful for reducing pigmentation in the skin. The composition may further include other depigmenting agents such as nicotinamide and its melanasome transfer-inhibiting derivatives, 3,3'-thiodipropanoic acid and its tyrosinase-inhibiting derivatives, or resorcinol and its tyrosinase-inhibiting derivatives, in a topically acceptable vehicle.

3 Claims, No Drawings

TOPICAL COMPOSITIONS AND METHODS FOR SKIN LIGHTENING

RELATED APPLICATIONS

This application is a U.S. National Phase application to International Application No. PCT/US2014/058246, filed Sep. 30, 2014. The entirety of which is incorporated by reference herein for all purposes.

FIELD OF INVENTION

The invention relates generally to cosmetic and dermatological compositions and methods for reducing pigmentation in human integuments. More particularly, the invention provides topical compositions and associated methods for treatment of hyperpigmentation or reduction of unwanted pigmentation. The compositions may be applied topically to skin to reduce pigmentation in the area of application.

BACKGROUND

The color of human skin is due primarily to the production of melanin by specialized cells in the skin called melanocytes through a process known as melanogenesis. The synthesis of melanin is a complex process involving several biochemical pathways. It is generally recognized that pigmentation may accompany inflammatory processes. Histamine is an agent involved in the inflammatory response which is reported to increase tyrosinase activity in human melanocytes, with the effects being completely inhibited by histamine antagonists such as famotidine. Histamine is postulated to induce melanogenesis in human cultured melanocytes by protein kinase A activation via $H_2$ receptor. See Yoshida, M. et al., Journal of Investigative Dermatology (2000) 114, 334-342, the contents of which are incorporated by reference herein. Recently, the expression of histamine receptors on melanocyte cells has been reported. See Salim, S. et al., J Recept Signal Transduct Res. 2011 April; 31(2): 121-31, the contents of which are incorporated by reference herein. However, the use of histamine antagonists to reduce pigmentation has received little attention to date.

Known depigmenting agents, such as hydroquinone and kojic acid, act as inhibitors of tyrosinase, an enzyme that has its catalytically active domain within organelles known as melanosomes. Tyrosinase converts phenols, including tyrosine, to ortho-quinones which are subsequently converted to melanin within the melanosomes. Other skin lighteners, such as plasminogen-activated receptor, act by disrupting the transfer of the melanosomes from melanocytes to the keratinocytes where melanin is deposited. While skin lighteners such as hydroquinone and kojic acid have found some utility in cosmetic and dermatological products, there remains a continuing need for products that effectively reduce pigmentation of skin particularly through mechanisms that may be complementary to those mentioned above to promote enhanced efficacy and/or synergies of combinations of depigmenting agents. It is therefore an object of the invention to provide compositions and methods for reducing pigmentation in human skin, including, for example, treatment of hyperpigmentation, unwanted pigmentation, age spots, liver spots, freckles, and the like.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF DISCLOSURE

In accordance with the foregoing objectives and others, the invention provides compounds, topical compositions and methods for reducing pigmentation in human skin. Without wishing to be bound by any theory, it is believed that the compounds of the invention are histamine receptor (e.g., $H_1$, $H_2$, $H_3$ and/or $H_4$ receptor) antagonists effective to reduce histamine-induced pigmentation in human skin. In some implementations, new $H_2$ receptor antagonists are provided. The compositions and methods may treat hyperpigmentation conditions, including those associated with UV damage, inflammation, and chronological aging, including without limitation treating, ameliorating, diminishing the appearance of, or preventing age spots, liver spots, freckles, mottled and discrete pigmentation, melasma and the like. The compositions and methods are also useful for reducing otherwise unwanted pigmentation, including overall lightening of the skin, as well as improving signs of chronological, environmental, or UV skin aging.

Various non-limiting embodiments of the invention are described below. It will be understood that throughout these embodiments, the term "reducing pigmentation" includes reducing, lessening, or diminishing the appearance of hyperpigmentation, including freckles, sun spots, age spots, etc., as well as lightening skin that may or may not be affected by hyperpigmentation. Reference to human skin in each of these embodiments, includes without limitation, skin of the face, neck, arms, hands, legs, etc.

The compounds of the invention have been found to be human histamine receptor antagonists (in particular, at the $H_2$ receptor) and thus are expected to reduce pigmentation, including histamine-induced pigmentation. of human integuments such as skin. In some embodiments, the compounds are histamine $H_2$ receptor antagonists, although it is contemplated that the compounds may act on any of $H_1$, $H_2$, $H_3$, or $H_4$ receptors or have non-specific activity (e.g., antagonist activity) across two or more of these receptors. However, it will be understood that the precise mechanism of action of the compounds is not intended to limit the invention unless otherwise indicated. The compounds of the invention are contemplated to be beneficial in reducing pigmentation and/or treating hyperpigmentation regardless of the mode of action.

In one aspect of the invention, topical compositions are provided for reducing pigmentation of human integuments (e.g., skin) comprising, in a topically acceptable vehicle (e.g., a water-in-oil, or oil-in-water emulsion or an aqueous serum), an effective amount (e.g., from about 0.0001% to about 0.01%, or to about 0.1%, or to about 1%, or to about 10% by weight) of a compound (e.g., an $H_2$ antagonist compound) according to formula (I):

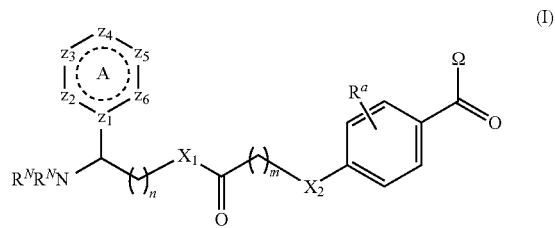

In the compound of formula (I), $R^N$ may be independently selected at each occurrence (i.e., they may be the same or different from one another) from hydrogen or saturated or unsaturated $C_1$-$C_{12}$ hydrocarbons, including, without limitation saturated or unsaturated aliphatic $C_1$-$C_{12}$ hydrocarbons (e.g., $C_1$-$C_4$ alkyl such as methyl, ethyl, propyl, butyl, etc.); aromatic $C_1$-$C_{12}$ hydrocarbons (e.g., phenyl, tolyl, etc.); aliphatic $C_1$-$C_{12}$ heterocycles, aromatic $C_1$-$C_{12}$ heterocycles, or combinations thereof (e.g., alkyl-aryl groups including benzyl); each of the foregoing optionally containing from 1-8 (or 1-3) heteroatoms selected from halogen, O, N, and S, and wherein any two groups $R^N$ may together form a three- to six-membered ring (e.g., piperidine, morpholine, piperazine, etc.). In one embodiment, two groups $R^N$ together with the nitrogen atom from a piperidine ring.

$R^a$ may be selected from hydrogen, —F; —Cl; —Br; —I; —OH, —OR*; —NH₂; —NHR*; —N(R*)₂; —N(R*)₃⁺; —N(R*)—OH; —N(→O)(R*)₂; —O—N(R*)₂; —N(R*)—O—R*; —N(R*)—N(R*)₂; —C=N—R*; —N=C(R*)₂; —C=N—N(R*)₂; —C(=NR*)—N(R*)₂; —SH; —SR*; —CN; —NC; —(C=O)—R*; —CHO; —CO₂H; —CO₂⁻; —CO₂R*; —(C=O)—S—R*; —O—(C=O)—H; —O—(C=O)—R*; —S—(C=O)—R*; —(C=O)—NH₂; —(C=O)—N(R*)₂; —(C=O)—NHNH₂; —O—(C=O)—NHNH₂; —(C=S)—NH₂; —(C=S)—N(R*)₂; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)₂; —N(R*)—C(=S)—N(R*)₂; —SO₂—R*; —O—S(=O)₂—R*; —S(=O)₂—OR*; —N(R*)—SO₂—R*; —SO₂—N(R*)₂; —O—SO₃—; —O—S(=O)₂—OR*; —O—S(=O)—OR*; —O—S(=O)—R*; —S(=O)—OR*; —S(=O)—R*; —NO; —NO₂; —NO₃; —O—NO; —O—NO₂; —N₃; —N₂—R*; —N(C₂H₄); —Si(R*)₃; —CF₃; —O—CF₃; —PR*₂; —O—P(=O)(OR*)₂; —P(=O)(OR*)₂; $C_1$-$C_8$ perfluoroalkyl; an aliphatic $C_1$-$C_8$ hydrocarbon radical; a $C_1$-$C_8$ aromatic hydrocarbon radical; or a $C_1$-$C_8$ heteroaryl radical. The phenyl rings to which $R^a$ is attached may comprise from 0-4 (or 0, 1, 2, 3, or 4) groups $R^a$, which will be independently selected at each occurrence.

$X_1$ and $X_2$ are independently selected from oxygen, sulfur, NR*, or CR*R* (typically, $X_1$ and/or $X_2$ is NH).

R* is independently, at each occurrence, hydrogen or a straight chained, branched, or cyclic $C_{1-20}$ (e.g., $C_{1-10}$ or $C_{1-6}$, or $C_{1-4}$, or $C_{1-3}$) hydrocarbon radical, which may be saturated, partially unsaturated, or aromatic, each of which may be optionally substituted with 1-6 (e.g., 1-4 or 1-3) heteroatoms selected from nitrogen, oxygen, sulfur, or halogen, including, without limitation, methyl, ethyl, propyl, butyl, etc.

Ring "A" is a five or six-membered optionally aromatic ring, $z_1$ is —C—, —N—, —NL₁-, or —CL₁-; and $z_2$-$z_6$ are independently selected from —N—, —NH—, —NR*—, —NL₁-, —O—, —S—, —CH—, —CR—, —CR*—, and in the case where ring "A" is a five membered ring, $z_4$ is a bond (i.e., it is absent); and where $L_1$ is a linking moiety that forms a linkage between ring A and the chain, where $L_1$ is group —$X^a$—(CH₂)ᵣ—(CH=CH)ₛ—$X^b$—(CH₂)ᵧ—(CH=CH)ᵤ—$X^c$—, where $X^a$, $X^b$, and $X^c$ are independently a bond (i.e., absent), —O—, —S—, —NH—, —NR*— and "r," "s," "y," and "z" are independently at each occurrence integers from 0-2.

Ω is selected from H, R*, OH, OR*, or NR^N R^N, wherein $R^N$ and R* are as defined above. Ω may be, for example, a group R* including without limitation lower alkyl (e.g., methyl, ethyl, propyl, butyl, pentyl and hexyl), phenyl, benzyl, each of which may include from 0-4 heteroatoms selected from O, N, S, and halogen, or may include a group $R^a$.

n and m are independently integers from 0-6, (e.g., 1-3) and in some embodiments n and m are each 1.

In another implementation, topical compositions are provided comprising, in a topically acceptable vehicle (e.g., an emulsion or serum), an effective amount (e.g., from about 0.0001% to about 0.01%, or to about 0.1%, or to about 1%, or to about 10% by weight) of a compound (e.g., an H₂ antagonist compound) having the structure of formula (II):

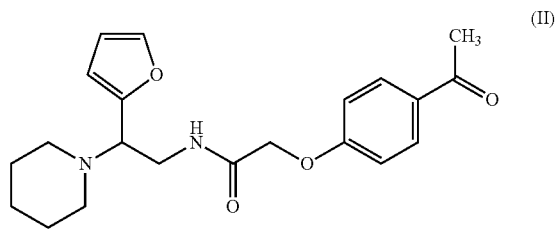 [SMILES: CC(=O)c1ccc(OCC(=O)NCC(c2ccco2)N2CCCCC2)cc1]

(II)

Topically acceptable salts (e.g., acid addition salts) of the compounds of formulas (I) or (II) are also suitable. The compositions of the invention typically comprise a vehicle, for example a water-in-oil or oil-in-water emulsion, which may further include various adjuvants such as thickeners, emulsifiers, gellants, emollients, humectants, UV absorbers, antioxidants, pH adjusters, chelators, film formers, preservatives, colorants, fragrances, and the like. The adjuvants may comprise, individually or collectively, from about 0.00001% to about 98% by weight of the composition. The topical preparations of the invention may further include one or more additional active agents, such as a retinoid (e.g., retinol, retinyl palmitate, retinyl acetate, retinaldehyde, retinoic acid, etc.), and antioxidant (e.g., ascorbic acid, thiodipropionic acid or esters thereof, including dilauryl thiodipropionate), α-hydroxy acids (e.g., glycolic acid), collagenase inhibitors, anti-inflammatories, anti-acne agents, salicylic acid and derivatives, depigmenting agents, N-acetyl tyrosinamide, and botanicals, to name a few. In some embodiments, the compounds of formula (I) or (II) are provided in combination with at least one additional depigmenting agent, such as a tyrosinase inhibitor or a melanosome transfer inhibitor. In one embodiment, the compositions include one or more of hydroquinone, kojic acid, salicylic acid or derivatives, thiodipropionic acid, and retinoids. Additional actives may individually or collectively comprise from about 0.0001% to about 20% by weight of the composition.

Topical compositions comprising a compound of formula (I) or (II) may be applied for a time sufficient to achieve a reduction in pigmentation in the area of application (e.g., application at least once or twice daily for at least one week, at least two weeks, at least four weeks, or at least eight weeks or longer. In some embodiments, the compositions are applied daily to achieve and/or maintain a reduction in pigmentation in the skin.

In one aspect of the invention, a method for reducing pigmentation in human skin is provided comprising topically applying the compound of formula (I) or (II) to skin. Without wishing to be bound by any particular theory, it is believed that the compounds of formula (I) or (II) act as histamine receptor (e.g., H₂ receptor) antagonists i.e., block or dampen histamine-mediated responses, which results in suppression of post-inflammation induced melanogenesis and production of melanin in the skin, thus reducing or diminishing pigmentation thereof.

These and other aspects of the present invention will be better understood by reference to the following detailed description and appended claims.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

All percentages given herein refer to the weight percentages of a particular component relative to the entire composition, including the vehicle, unless otherwise indicated. It will be understood that the sum of all weight % of individual components within a composition will not exceed 100%.

All terms used herein are intended to have their ordinary meaning unless otherwise provided. The phrases "cosmetically acceptable," "topically acceptable" and "dermatologically acceptable" are used interchangeably and are intended to mean that a particular component is generally regarding as safe and non-toxic for application to a human integument (e.g., skin) at the levels employed. The term "prevent," as used herein, includes delaying the onset of or progression of a particular sign of skin aging. The phrase "individual in need thereof" refers to a human that could benefit from improved dermal appearance or health, including males or females. In some embodiments, the individual in need thereof is a female. The term "skin" includes, without limitation, the lips, skin of the face, hands, arms, neck, scalp, and chest. As used herein, the term "consisting essentially of" is intended to limit the invention to the specified materials or steps and those that do not materially affect the basic and novel characteristics of the claimed invention, as understood from a reading of this specification.

The compositions may be used for reducing pigmentation and/or lightening areas of the human integumentary system, including but not limited to, keratinous surfaces such as skin, hair, lips, and nails. The compositions are typically topical compositions that once applied to the integumentary system result in a lightening (e.g., de-pigmenting) of the integument to which it is applied.

In some embodiments, the compositions and methods are for the treatment of hyperpigmentation, which includes eradicating, reducing, ameliorating, or reversing a degree of subject pigmentation. The hyper-pigmentation may result from increased presence of one or more of the different types of melanin biosynthesized in skin and/or follicles and deposited in hair or skin, relative to a subject's baseline pigmentation. The compositions may be applied directly to a localized site of hyper-pigmentation.

In some embodiments, the compositions and methods are for lightening skin, which includes eradicating, reducing, ameliorating, and/or reversing a baseline degree of subject pigmentation. Lightening skin may be measured by observing changes in Fitzpatrick scale value of a subject. The Fitzpatrick Scale (aka, Fitzpatrick skin typing test or Fitzpatrick phototyping scale) is a numerical classification schema for the color of skin, and remains a recognized tool for dermatologic research into the color of skin. The Fitzpatrick Scale measures several components, including Genetic Disposition, Reaction to Sun Exposure and Tanning Habits, and classifies skin into six types: Type I (scores 0-7) refers to white, very fair skin, freckles, typical albino skin, that always burns, never tans; Type II (scores 8-16) refers to white, fair skin, that usually burns, or tans with difficulty; Type III (scores 17-24) refers to beige, which is very common, and which sometimes suffers mild burn, gradually tans to a light brown; Type IV (scores 25-30) refers to beige skin with a brown tint, which is typical of Mediterranean Caucasian skin, and which rarely burns, tans with ease to a moderate brown; Type V (scores over 30) refers to dark brown skin which very rarely burns, tans very easily; Type VI refers to black skin that never burns, tans very easily, and is deeply pigmented. In some embodiments of the invention, the treatments are capable of changing the treated area of skin by at least one or at least two skin type on the Fitzpatrick scale. When lightening skin, it may be desirable to apply the composition over a large area of skin (e.g., over the entire skin of the face).

The compositions and methods of the invention are also contemplated to be useful for treating, reducing, ameliorating, improving, alleviating, and/or eliminating the dermatological effects of aging and/or environmental stress. The compositions and methods are suitable for use in treating dermatological conditions of the skin (including excessive or unwanted pigmentation) in numerous areas of the body, including, without limitation, the face, forehead, lips, neck, arms, hands, legs, knees, feet, chest, back, groin, buttocks, thighs, and the like. In one embodiment, the compositions are applied to the face, chest, arms and/or hands.

Specific benefits which may be achieved include, but are not limited to, reducing pigmentation of dark or hyperpigmented skin; reducing age spots or liver spots; reducing pigmented birthmarks, sun damage, tans, pigmented acne marks, scars; evening out or optimizing skin discoloration; decreasing the appearance of dark circles under the eyes; treating melasma, cholasma, freckles, after-burn scars, yellowing of skin, and post-inflammation and post-injury hyperpigmentation; lightening hair on the scalp, legs, face, and other areas where whitening and color reduction are desired; and removing or reducing nail stains.

The compounds, compositions and methods of use thereof are not limited by any particular characterization of the physiological and/or chemical effects of lightening agents. Various skin lightening pathways are known and include, for example, those that occur by decreasing melanogenesis by decreasing tyrosinase activity in melanocytes as well as inhibiting melanosome maturation. However, the lightening agents used in the present compositions and methods are believed to lighten skin by acting as histamine receptor (e.g., $H_1$ and/or $H_2$) antagonists, i.e., blocking or dampening histamine-mediated responses, which results in suppression of post-inflammation induced melanogenesis and production of melanin in the skin, thus reducing or diminishing pigmentation thereof.

The compounds of the invention (e.g., $H_2$ receptor antagonist compounds) may have the structure of formula (I):

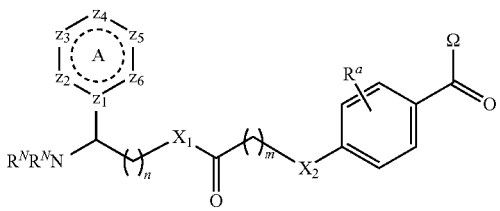

(I)

$R^N$ may be independently selected at each occurrence from hydrogen or $C_1$-$C_{12}$ hydrocarbons. The $C_1$-$C_{12}$ hydrocarbons include, without limitation, saturated or unsaturated aliphatic $C_1$-$C_{12}$ hydrocarbons (e.g., alkyl groups such as methyl, ethyl, propyl, butyl, etc.); aromatic $C_1$-$C_{12}$ hydrocarbons (e.g., phenyl, tolyl, etc.); aliphatic $C_1$-$C_{12}$ heterocycles, aromatic $C_1$-$C_{12}$ heterocycles, or combinations thereof. In some embodiments, the $C_1$-$C_{12}$ hydrocarbons are $C_1$-$C_{12}$ alkyl, or $C_2$-$C_{12}$ alkenyl, or $C_2$-$C_{12}$ alkynyl or $C_6$-$C_{12}$ aryl, or $C_6$-$C_{12}$ alkyl-aryl or aryl-alkyl groups. The $C_1$-$C_{12}$ hydrocarbons optionally contain from 1-8 (or 1-4, or 1-3) heteroatoms selected from halogen (e.g., F, Cl, Br, etc.), O, N, and S (including combinations thereof). In some embodiments, two groups $R^N$ on the same nitrogen atom may together form a three- to six-membered ring (e.g., 3, 4, 5, or 6 members) including the nitrogen atom.

$R^a$ may be located on any available position on the ring to which they are attached and may be present on 0-4 of the available positions and independently selected at each occurrence. $R^a$ may be independently selected at each occurrence from hydrogen, —F; —Cl; —Br; —I; —OH, —OR*; —NH$_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —CO$_2$H; —CO$_2^-$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S)—N(R*)$_2$; —SO$_2$—R*; —O—S(=O)$_2$—R*; —S(=O)$_2$—OR*; —N(R*)—SO$_2$—R*; —SO$_2$—N(R*)$_2$; —O—SO$_3^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; $C_1$-$C_8$ perfluoroalkyl; an aliphatic $C_1$-$C_8$ hydrocarbon radical; a $C_1$-$C_8$ aromatic hydrocarbon radical; or a $C_1$-$C_8$ heteroaryl radical. In some embodiments $R^a$ will be present at 0, 1, 2, 3, or 4 different positions on the ring.

$X_1$ and $X_2$ are independently selected from oxygen, sulfur, NR*, or CR*R*, but typically, $X_1$ and/or $X_2$ is NH or NR*.

R* is independently at each occurrence selected from hydrogen or a straight chained, branched, or cyclic $C_{1-20}$ (e.g., $C_{1-12}$ or $C_{1-6}$, or $C_{1-4}$, or $C_{1-3}$) hydrocarbon radical, which may be saturated, partially unsaturated (e.g., one, two, or three double or triple bonds), or aromatic (e.g., heteroaromatic), each of which may be optionally substituted with 1-6 (e.g., 1-4 or 1-3) heteroatoms selected from nitrogen, oxygen, sulfur, or halogen. Examples of R* include $C_1$-$C_{12}$, or $C_1$-$C_6$, or $C_1$-$C_4$ alkyl, including methyl, ethyl, propyl (e.g., n-propyl or iso-propyl), butyl, pentyl, hexyl, etc.; $C_6$-$C_{12}$ aryl groups including phenyl; $C_7$-$C_{12}$ aryl-alkyl or alkyl-aryl groups like benzyl, tolyl, etc.

Ring "A" is a five or six-membered optionally aromatic ring, $z_1$ is —C—, —N—, —NL$_1$-, or —CL$_1$-; and $z_2$-$z_6$ are independently selected from —N—, —NH—, —NR*—, —O—, —S—, —CH—, —CR—, —CR*—, and in the case where ring "A" is a five membered ring, $z_4$ is a bond (i.e., it is absent); and where L$_1$ is group —X$^a$—(CH$_2$)$_r$—(CH=CH)$_s$—X$^b$—(CH$_2$)$_y$—(CH=CH)$_z$—X$^c$—, where X$^a$, X$^b$, and X$^c$ are independently a bond (i.e., absent), —O—, —S—, —NH—, —NR*— and "r," "s," "y," and "z" are independently at each occurrence integers from 0-2.

Ω is selected from H, R*, OH, OR*, or NR$^N$R$^N$, wherein R$^N$ and R* are as defined above.

n and m are independently integers from 0-6, (e.g., 1-3). Typically one or more (and sometimes all) of n and m are 1.

In certain implementations, $R^a$ may independently be selected, at each occurrence, from hydrogen, methyl, ethyl, propyl, butyl, pentyl, and hexyl. In certain implementations, $R^a$ is a hydrogen at all occurrences. In some embodiments, $R^a$ is present at one, two, three or four positions on the ring to which it is attached.

In certain implementations, two groups $R^N$ located on the same nitrogen atom may form a ring together with the nitrogen atom to which they are attached. In one embodiment, two groups $R^N$ form a six-membered ring. The six-membered ring may be, for example, piperidine, morpholine, thiomorpholine, piperazine, etc. In another embodiment, two groups $R^N$ form a five-membered ring together with the nitrogen atom to which they are attached. The five membered rings may be, for example, pyrrole, pyrrolidine, imidazolidine, oxazolidine, thiazolidine, etc. In another embodiment two groups $R^N$ are hydrogens.

In certain implementations, n and m are independently integers from 0-5. In one embodiment, n and m are independently integers from 1-4. In another embodiment, n and m are independently integers from 1-2. In another embodiment, n and/or m are 1.

In certain implementations, Ω may be selected from methyl, ethyl, propyl, butyl, pentyl, and hexyl. In certain implementations, Ω is methyl.

In one embodiment, wherein $z_4$ is a bond (i.e., it is absent), ring "A" may be selected from the group consisting of:

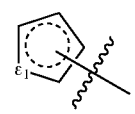

(i)

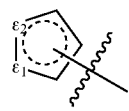

(ii)

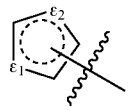

(iii)

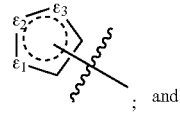

(iv)

; and

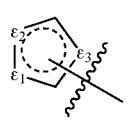
(v)

wherein $\epsilon_1$, $\epsilon_2$, and $\epsilon_3$, are independently selected from N, NH, NR*, S, and O; with the proviso that where the point of attachment is $\epsilon_1$, $\epsilon_2$, or $\epsilon_3$, then that position represents N; and wherein carbon atoms which are not the point of attachment may be optionally substituted with a group R*; and wherein the dashed circles indicate that each ring may comprise zero, one, or two double bonds. In some embodiments, ring "A" is a ring Q having the form:

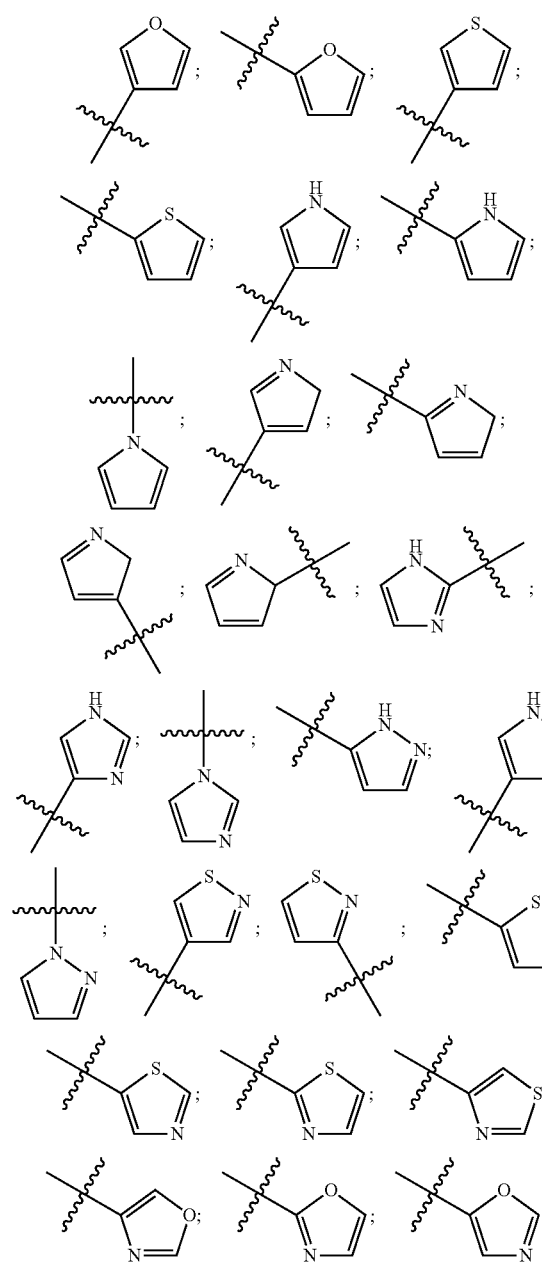

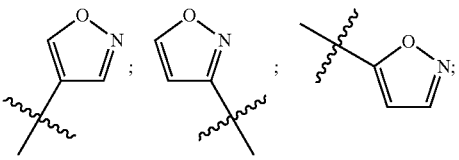

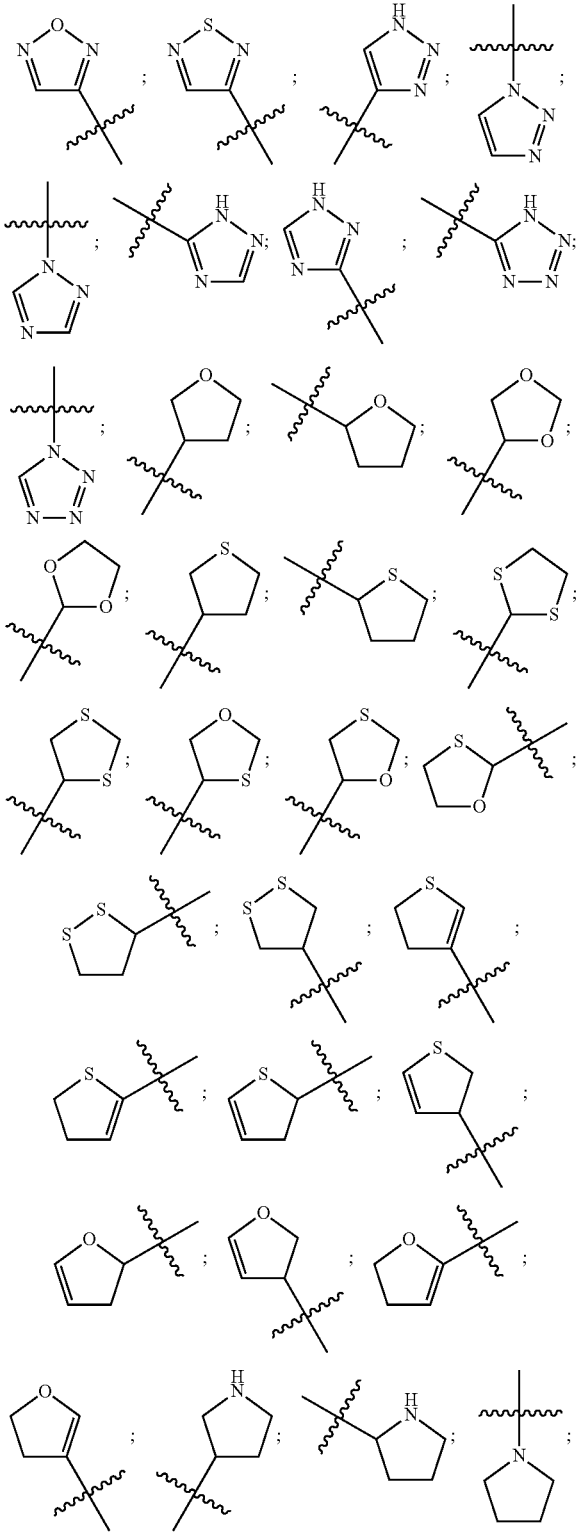

-continued

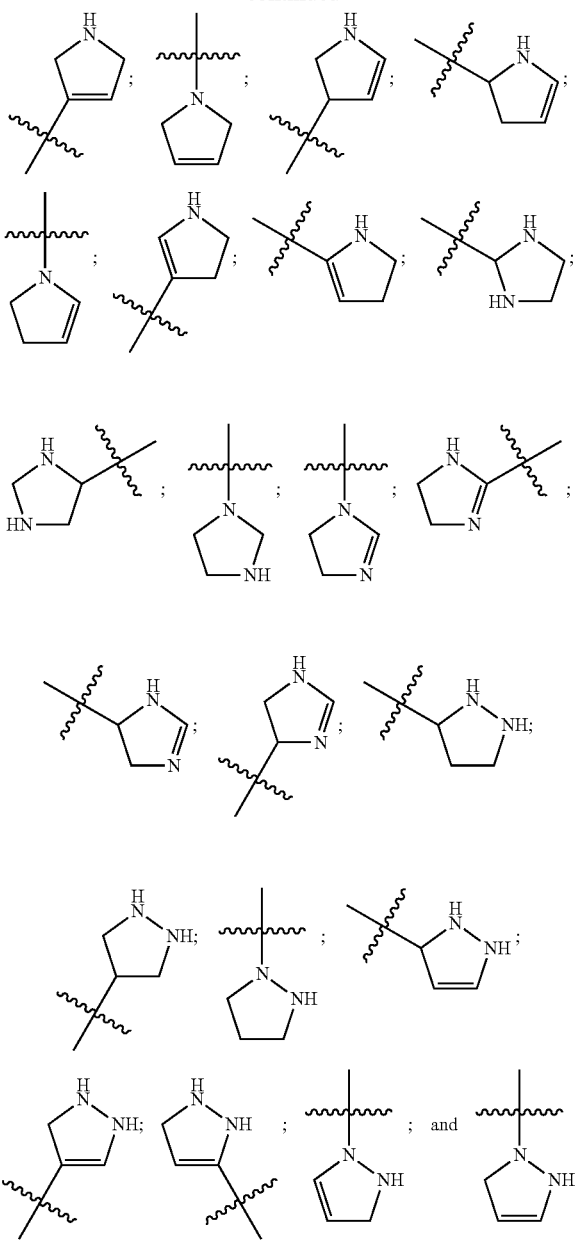

wherein any available site on the ring "A" or "Q" may be optionally substituted with a group R (e.g., methyl, methoxy, halo, hydroxyl, amino, etc.). In some embodiments, ring "A" is:

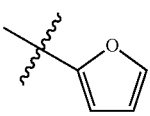 [SMILES: *c1ccco1]

In another embodiment, ring "A" is a six membered aromatic ring.

In another implementation, topical compositions are provided comprising a compound having the structure of formula (II):

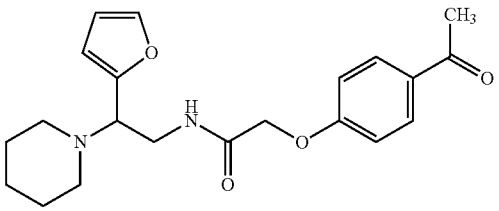

(II)

Topically acceptable salts of the compounds of formulas (I) or (II) are also suitable. Salts will typically be acid addition salts formed by the reaction of a compound of formulas (I) or (II) with an inorganic or an organic acid. Inorganic acids include mineral acids such as HCl and $H_2SO_4$, and the like.

The compositions according to the invention can be formulated in a variety of forms for topical application and will typically comprise from about 0.000001% by weight to about 20% by weight of one or more compounds according to Formula (I) or (II), and preferably will comprise from about 0.00001% by weight to about 10% by weight, and more preferably from about 0.0001% by weight to about 5% by weight of the composition. In one embodiment, the active will comprise from about 0.0001% by weight to about 0.1% by weight or to about 0.5% by weight or to about 1% by weight of the composition. The compositions will comprise and effective amount of the compound according to Formula (I) or (II), by which is meant an amount sufficient to have a melanogenesis-suppressive effect in a given area of skin when topically applied thereto.

It may be advantageous to employ the compound of formulas (I) or (II) together (including simultaneous or serial application) with other skin lightening agents such as tyrosinase inhibitors and/or melanosome transfer inhibitors. Special mention may be made of hydroquinone and the monobenzyl ether thereof; hydroquinone-beta-D-glucopyranoside; retinoids (e.g., retinol or retinoic acid); tretinoin; nicotinamide, niacinamide, hydroxystilbenes, flavonoids, resveratrol, oxyresveratrol, piceid-glucoside, rhapontigenin, rhaponticin, azelaic acid; Kojic acid (5-hydroxy-4-pyran-4-one-2-methyl); melatonin, Mequinol (4-hydroxyanisole); soy protein (e.g., Bowman Birk inhibitor (BBI) and/or soybean trypsin inhibitor (STI)) and other serine protease inhibitors; paper mulberry extract; Glutathione, glycolic acid, Glabridin (licorice extract); *Arctostaphylos patula* and *Arctostaphylos viscida* extracts; gentisic acid, *Glycyrrhiza glabra* and its derivatives; *Chlorella vulgaris* extract; Magnesium-L-ascorbyl-2-phosphate (MAP); 4-Isopropylcatechol; Arbutin; Aleosin; Linoleic acid; N-acetyl-4-S-cysteaminylphenol and N-propionyl-4-S-cysteaminylphenol; N-acetyl glucosamine; and Tranexamic acid (trans-4-aminomethylcyclohexanecarboxylic acid); bearberry extract, ascorbic acid and/or its derivatives, salicylic acid and derivatives, *perilla* extract (e.g., in U.S. Pat. No. 5,980,904 and Japanese Publications Nos. 07025742, 07187989, 10265322, 2001163759, and 2001181173, incorporated herein by reference), coconut fruit extract (Japanese Patent No. 2896815B2, incorporated by reference herein), coconut water, green tea extract, ginseng, gingko, gallic acid, α-tocopherol and calcium influx inhibitors, to name a few. Any of the tyrosine inhibitors disclosed in KR 2005095167; JP 2003252743; and JP 61260009, incorporated herein by reference, may be included, in some embodiments. In another embodiment of the invention, the compositions may include any of the following ingredients, alone or in combination: nilopala; patanga; chandana; ushira; manjshta; kumkuma; laksa; padmakesara; padmaka; yashtimadhu; ajakshira; ksheera; nyagrodhapada; and/or lodhra. These additional depigmenting agents may individually or collectively comprise from about 0.0001% or about 0.01% to about 10% or about 20% by weight of the composition.

The cosmetically acceptable vehicle may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. As used herein, the term "oil" includes silicone oils unless otherwise indicated. The emulsion may include an emulsifier, such as a nonionic, anionic or amphoteric surfactant, or a gallant, typically in an amount from about 0.001% to about 5% by weight.

The cosmetically acceptable vehicle may include water; vegetable oils; mineral oils; ester oils such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, preferably organomodified derivatives including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise from about 50% to about 99% by weight of the composition.

In one embodiment of the invention, the compositions may include additional skin actives, including but not limited to, retinoids, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors, to name but a few. The amounts of these various ingredients are those conventionally used in the cosmetic field to achieve their intended purpose, and range individually or collectively typically from about 0.001 wt % to about 20 wt % by weight of the composition. The nature of these ingredients and their amounts must be compatible with the production and function of the compositions of the disclosure.

Exemplary anti-aging components include, without limitation, botanicals (e.g., *Butea frondosa* extract); phytol; phytonic acid; retinoids; hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

Exemplary retinoids include, without limitation, retinoic acid (e.g., all-trans, or 9-cis, or 13-cis), and derivatives thereof, retinaldehyde, retinol (Vitamin A) and esters thereof, such as retinyl palmitate, retinyl acetate and retinyl propionate, and salts thereof. Particular mention may be made of retinol. When present, the retinoids will typically be included in amounts from about 0.0001% to about 5% by weight, more typically from about 0.01% to about 2.5% by weight, or from about 0.1% to about 1.0% by weight. Compositions according to this embodiment will typically include an antioxidant such as ascorbic acid and/or BHT and/or a chelating agent such as EDTA or a salt thereof (e.g., disodium EDTA).

In another embodiment, the topical compositions of the present invention may also include one or more of the following: a skin penetration enhancer; an emollient, such as isopropyl myristate, petrolatum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; a sunscreen, such as avobenzone or octyl methoxycinnamate; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Antioxidants may comprise, individually or collectively, from about 0.001% to about 10% (w/w), or from about 0.01% to about 5% (w/w) of the total weight of the composition.

Other additives include: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethyl-cellulose, carbombers, and vegetable gums such as xanthan gum; gelling agents, such as ester-terminated polyester amides; structuring agents; metal chelating agents such as EDTA or salts thereof; pigments; colorants; and pH adjusters (citric acid, ethanolamine, sodium hydroxide, etc.). The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders.

In addition, the compositions contemplated by this disclosure can include one or more compatible cosmetically acceptable adjuvants commonly used and known by the skilled practitioner, such as colorants, pearls, chromalites, micas, pigments, dyes, fragrances, emollients, humectants, preservatives, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and botanicals. The topical compositions of the present disclosure may also include a skin penetration enhancer, a surface smoother, a skin plumper, an optical diffuser, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of these various substances are those that are conventionally used in the cosmetic or pharmaceutical fields, for example, they can constitute from about 0.01% to about 20% of the total weight of the composition.

A sunscreen may be included to protect the skin from damaging ultraviolet rays. In an illustrative embodiment of the present disclosure, the sunscreen provides both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1 wt % to about 30 wt % of the total weight of the composition.

In one embodiment, the topical composition will have a pH range from 1 to 13, with a pH in the range of from 2 to 12 being typical. In some embodiment, the composition will have a pH in the range of from 3.5 to 7 or from 7-10.5. In some embodiments, the pH will be in the range of 3-4, or 4-5, or 5-6, or 6-7, or 7-8, or 8-9, or 9-10, or 10-11, or 11-12. Suitable pH adjusters such as sodium hydroxide, citric acid and triethanolamine may be added to bring the pH within the desired range.

Another embodiment of the present disclosure is directed to the delivery of the described compositions by the use of targeted delivery systems, for example, liposomes, microspheres (see, e.g., U.S. Pat. No. 5,770,222 to Unger et al.), and the like, so that the components and/or active constituents can more readily reach and affect the subcutaneous layer of the area of application, e.g., face or neck, or the other area of the skin.

The compositions may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

In certain embodiments, the cosmetic compositions described herein can be used to treat and/or prevent hyper-pigmentation of skin and/or of the hair, for example, to lighten skin or hair. In some embodiments, a composition is topically applied to the skin or hair, for example to an area of hyper-pigmented skin or hair. Hyper-pigmentation includes any coloration of an individual's skin or hair that is darker than desired by the individual and that is caused by melanocytes. Such unwanted pigmentation may also be called discoloration. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also include areas of tanned skin, for example, skin tanned due to UV exposure. Hyper-pigmented hair includes any shade of hair that is darker than desired.

Treating hyper-pigmentation or hyper-pigmented skin/hair refers to eradicating, reducing, ameliorating, or reversing one or more of the unwanted features associated with hyper-pigmentation, such as producing a perceptible lightening of the skin or hair in the affected area. Lightening hyper-pigmented areas of the skin may be desirable, in one embodiment, in diminishing age spots; lightening a suntan; evening or optimizing skin tones, e.g., in areas of mottled hyper-pigmentation; in treating melasmic and chloasmic patches, freckles, after-burn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

Topical compositions comprising a compound (I) or (II) may be applied for a time sufficient to achieve a reduction in pigmentation in the area of application. This may entail topical application at least once daily for at least one week, at least two weeks, at least four weeks, or at least eight weeks or more. In some embodiments, the compositions are applied directly to a site of hyperpigmentation on the skin (i.e., directly onto an age spot or sun spot). In some embodiments, the compositions are applied daily to achieve and/or maintain a reduction in pigmentation in the skin. In one embodiment, the compositions of the invention will be applied to the skin in an amount from about 0.001 to about 100 mg/cm$^2$, more typically from about 0.01 to about 20 mg/cm$^2$, or from about 0.1 to about 10 mg/cm$^2$.

The present inventive compositions provide for products, especially skin care and cosmetic products that lighten skin in need thereof. Skin in need thereof includes, but is not limited to, dark complexions, hyperpigmented skin, post-inflammation hyperpigmented skin, age spots, liver spots, discolored or uneven skin, dark circles under the eyes for example, skin having melasma, cholasma, freckles, after-burn scars, post-injury hyperpigmented skin, skin, scalp, legs, face, and other areas where whitening or color reduction are desired, yellowed skin, stained nails, and the like.

One embodiment of the invention relates to methods of applying an effective amount of the lightening composition described herein, to lighten an affected area of the skin as used herein. The lightening composition may remain on the affected area in need of lightening or may be rinsed off or otherwise removed depending on the application. In order to maintain the desired lightening effect, the protocol should be continued for as long as the lightening effect is desired. Once the application of the lightening composition is discontinued, the desired lightening effect may also diminish.

In another aspect of the invention, the compositions are applied topically to improve the aesthetic appearance of human skin. The method comprises topically applying to an area of the skin in need thereof a composition comprising an effective amount of a compound of Formula (I) or (II) for a time sufficient to improve the aesthetic appearance of said human skin. The compositions are topically applied to the skin in effective amounts, by which is meant an amount sufficient to achieve a measurable improvement in skin health or reduction in one or more dermatological signs of aging with daily (once, twice, etc.) administration, typically for a period of at least one week or more.

The aesthetic improvement of human skin may be an improvement of any attribute or characteristic of skin, including without limitation:

(a) treatment, reduction, and/or prevention of fine lines or wrinkles;

(b) reduction of skin pore size;

(c) improvement in skin thickness, plumpness, and/or tautness;

(d) improvement in skin smoothness, suppleness and/or softness;

(e) improvement in skin tone, radiance, and/or clarity;

(f) improvement in procollagen, and/or collagen production;

(g) improvement in maintenance and remodeling of elastin;

(h) improvement in skin texture and/or promotion of retexturization;

(i) improvement in skin barrier repair and/or function;

(j) improvement in appearance of skin contours;

(k) restoration of skin luster and/or brightness;

(l) replenishment of essential nutrients and/or constituents in the skin;

(m) improvement of skin appearance decreased by aging and/or menopause;

(n) improvement in skin moisturization;

(o) increase in skin elasticity and/or resiliency;

(p) treatment, reduction, and/or prevention of skin sagging;

(q) improvement in skin firmness; and (r) reduction of pigment spots and/or mottled skin; and (s) improvement of optical properties of skin by light diffraction or reflection.

In a related implementation, a method is provided for the treatment of wrinkles and/or fine lines on the skin human skin (typically, skin of the face) comprising topically applying to an area of the skin in need thereof (e.g., applying to a wrinkle or fine line) a composition of Formula (I) or (II), for a time sufficient to improve the aesthetic appearance of said human skin. The treatment may be a least once or twice daily and may last for a period of at least four weeks, typically at least eight weeks or longer. The composition may optionally further comprise a retinoid (e.g., retinol or retinyl palmitate) and/or an alpha-hydroxy acid (e.g., glycolic acid) and/or a beta-hydroxy acid (e.g., salicylic acid or derivative) in amounts effective to improve the appearance of skin.

In a related aspect, methods are provided for enhancing the production of collagen or pro-collagen in human skin comprising topically applying to an area of the skin in need thereof (e.g., sagging skin, thinning skin, skin suffering from wrinkles and fine lines, etc.) a topical composition comprising a cosmetically acceptable vehicle, and an effective amount of a compound of Formula (I) or (II), for a time sufficient to improve the appearance thereof. The treatment may be a least once or twice daily and may last for a period of at least four weeks, typically at least eight weeks or longer. The composition may optionally further comprise a retinoid and/or an alpha-hydroxy acid (e.g., glycolic acid) and/or a beta-hydroxy acid (e.g., salicylic acid or a derivative) in amounts effective to improve the appearance of skin.

In yet another aspect of the invention, methods are provided for reducing the severity of, reducing the number of, or preventing or forestalling the onset of, wrinkles or fine lines on human skin comprising topically applying to an area of the skin in need thereof (e.g., wrinkled skin), an effective amount (e.g., 0.0001%-1% by weight, w/w) of a compound of Formula (I) or (II), in combination with an effective amount (e.g., 0.01%-5% by weight, w/w) of retinol and/or an effective amount (e.g., 0.001%-5% by weight, w/w) of an alpha-hydroxy acid (e.g., glycolic acid) and/or a beta-hydroxy acid (e.g., salicylic acid).

The invention provides a method for treating aging skin by topically applying a composition comprising a collagen-stimulating compound of Formula (I) or (II), typically in a cosmetically acceptable vehicle, over the affected area for a period of time sufficient to remediate, reverse, reduce, ameliorate, or prevent dermatological signs of aging. Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof. In some embodiments, each of the forgoing is associated with female skin.

In some embodiments, the compounds of Formulas (I) or (II) will be used to reduce the severity of fine lines or wrinkles, often in combination with retinol. The composition will typically be applied to the skin one, two, or three times daily for as long as is necessary to achieve desired results. The treatment regimen may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the cosmetic compositions of the invention will be applied to the skin in an amount from about 0.001 to about 100 mg/cm$^2$, more typically from about 0.01 to about 20 mg/cm$^2$, or from about 0.1 to about 10 mg/cm$^2$.

It is also contemplated that the compositions of the invention will be useful for treating thin skin by topically applying the composition to thin skin of an individual in need thereof. "Thin skin" is intended to include skin that is thinned due to chronological aging, menopause, or photodamage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals.

In one embodiment, the compositions of the invention are applied to human skin to reduce sebum production or improve the appearance of skin affected by cellulite, and/or reduce unwanted lipogenesis or increase lipolysis. In this embodiment, the compounds of Formulas (I) or (II) can be formulated in cosmetically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, *perilla* oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or longer. In one embodiment, the compositions are topically applied to treat acne.

In another embodiment, the compounds of Formulas (I) or (II) are intended for oral use, including for pharmaceutical use. Pharmaceutical formulations will include pharmaceutically acceptable carriers (i.e., diluents and excipients). The pharmaceutical compositions may be included in solid dosage forms, including compressed tablets and capsules, or in liquid or powder forms. Pharmaceutical dosage forms will typically include from about 0.5 mg to about 200 mg, or from about 1 mg to about 100 mg of the compound of Formulas (I) or (II). The dosage forms may be immediate release, in which case they will typically comprise a water-soluble or dispersible carrier such as microcrystalline cellulose, mannitol, hydroxypropyl methyl cellulose, PVP or the like, or may be delayed, sustained, or modified release, in which case they may comprise water-insoluble polymers such as cellulose ethers (e.g., ethylcellulose), alone or in combination with water soluble or dispersible polymers, to regulate the rate of dissolution of the dosage form in the stomach.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, §201(i).

EXAMPLES

The following example illustrates a specific aspect of the instant description. The example should not be construed as limiting, as the example merely provides specific understanding and practice of the embodiments and its various aspects.

Example 1

The Compound of Formula (II) was examined for its ability to reduce pigmentation in vitro in human melanocytes. Human epidermal melanocytes from dark-pigmented skin were seeded in 6-well dishes and grown using commercially available Medium 254, a sterile, liquid medium prepared with 200 μM calcium chloride for the culture of human epidermal melanocytes, supplemented with 1% Penicillin/Streptomycin and 1% Human Melanocyte Growth Supplement. Histamine, Diphenhydramine HCl and Compound II were added to the growth medium at the concentrations listed in Table 1 below. Corresponding controls were maintained without histamine, Diphenylhydramine HCl and Compound II. Four replicates were tested for each combination. After 8 days of incubation, melanin was collected and processed by washing the wells with IX phosphate-buffered saline (PBS), followed by addition of 200 μL of 2M NaOH to three of the four replicates, which are then scraped, pooled and boiled at 80° C. for an hour. Melanin absorption was then measured at 405 nm using a spectrophotometer.

Results are summarized in Table 1 below as percent change of melanin absorbance relative to vehicle control. A larger (positive or negative) percent change indicates a larger increase or reduction in melanin.

TABLE 1

| Compound | Concentration | % Pigmentation |
|---|---|---|
| Histamine | 5 μM | 58.75% |
| Diphenhydramine HCl | 5 μM | −38.75% |
| Compound (II) | 0.001% | −40.83% |
|  | 0.0001% | −10.40% |

As shown in Table 1, histamine produces a significant increase in pigmentation whereas the histamine antagonist diphenhydramine hydrochloride reduces pigmentation. At both concentrations tested, the compound of Formula (II) was effective to reduce pigmentation.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

The invention claimed is:

1. A method for reducing pigmentation of human skin comprising topically applying to an area of the skin in need thereof a composition comprising, in a topically acceptable vehicle, an effective amount of a compound having the structure of formula (I):

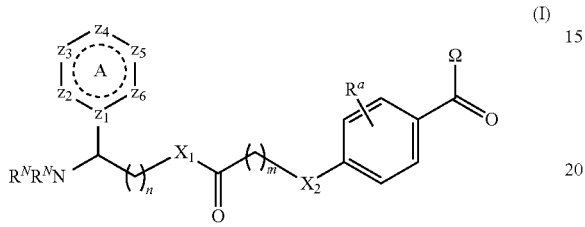

wherein, $R^N$ are independently selected at each occurrence from hydrogen or $C_1$-$C_{12}$ hydrocarbons, optionally containing from 1-8 heteroatoms selected from halogen, O, N, and S and combinations thereof; and wherein two groups $R^N$ on the same nitrogen atom may together form a three- to six-membered ring;

$R^a$ is independently selected from hydrogen, —F; —Cl; —Br; —I; —OH, —OR*; —NH$_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —CO$_2$H; —CO$_2^-$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S)—N(R*)$_2$; —SO$_2$—R*; —O—S(=O)$_2$—R*; —S(=O)$_2$—OR*; —N(R*)—SO$_2$—R*; —SO$_2$—N(R*)$_2$; —O—SO$_3^-$; —O—S(=O)$_2$—OR*; —O—S(=O)—OR*; —O—S(=O)—R*; —S(=O)—OR*; —S(=O)—R*; —NO, —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; $C_1$-$C_8$ perfluoroalkyl; an aliphatic $C_1$-$C_8$ hydrocarbon radical; a $C_1$-$C_8$ aromatic hydrocarbon radical; or a $C_1$-$C_8$ heteroaryl radical;

$X_1$ and $X_2$ are independently selected from oxygen, sulfur, or $NR^N$;

R* is independently at each occurrence hydrogen or a straight chained, branched, or cyclic $C_1$-$C_{20}$ hydrocarbon radical, optionally substituted with one or more groups $R^a$ or with 1-6 heteroatoms selected from nitrogen, oxygen, sulfur, or halogen and combinations thereof;

ring "A" is a five or six-membered optionally aromatic ring, $z_1$ is —C—, —N—, —NL$_1$-, or —CL$_1$-;

and $z_2$-$z_6$ are independently selected from —N—, —NH—, —NR—, —O—, —S—, —CH—, —CR—, —CR*—, and in the case where ring "A" is a five membered ring, $z_4$ is a bond (i.e., it is absent); where $L_1$ is group —V—(CH$_2$)$_r$—(CH=CH)$_s$—X$^b$—(CH$_2$)$_y$—(CH=CH)$_z$—X$^c$—, where X$^a$, X$^b$, and X$^c$ are independently a bond (i.e., absent), —O—, —S—, —NH—, —NR*— and "r," "s," "y," and "z" are independently at each occurrence integers from 0-2;

Ω is selected from H, R*, OH, OR*, or NR$^N$R$^N$, wherein R$^N$ and R* are as defined above;

and n and m are independently integers from 0-6;

and topically acceptable salts thereof, for a time sufficient to reduce the pigmentation of said human skin.

2. The method of claim 1, wherein the compound has the structure of formula (II):

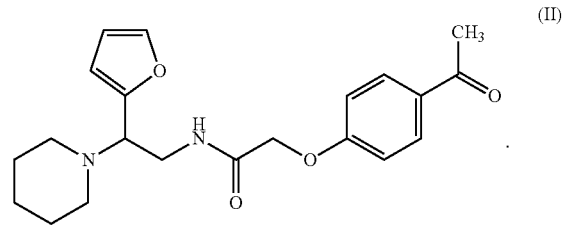 [SMILES: CC(=O)c1ccc(OCC(=O)NCC(c2ccco2)N2CCCCC2)cc1]

3. The method according to claim 1, wherein said composition is applied at least once daily for a period of at least four weeks.

* * * * *